(12) United States Patent
Fischbach (10) Patent No.: US 9,097,702 B2
(45) Date of Patent: Aug. 4, 2015

(54) PATHOLOGICALLY RELEVANT TUMOR MICROENVIRONMENTS FOR HIGH-THROUGHPUT DRUG SCREENING

(75) Inventor: Claudia Fischbach, Ithaca, NY (US)

(73) Assignee: Cornell University, Ithaca, NY (US)

( * ) Notice: Subject to any disclaimer, the term of this patent is extended or adjusted under 35 U.S.C. 154(b) by 1359 days.

(21) Appl. No.: 12/510,925

(22) Filed: Jul. 28, 2009

(65) Prior Publication Data

US 2010/0056390 A1 Mar. 4, 2010

Related U.S. Application Data (60) Provisional application No. 61/084,328, filed on Jul. 29, 2008.

(51) Int. Cl.
*C40B 30/06* (2006.01)
*C40B 50/06* (2006.01)
*G01N 33/50* (2006.01)
*B01J 19/00* (2006.01)
*C40B 60/08* (2006.01)

(52) U.S. Cl.
CPC ......... *G01N 33/5008* (2013.01); *B01J 19/0046* (2013.01); *C40B 60/08* (2013.01); *G01N 33/5011* (2013.01); *B01J 2219/0036* (2013.01); *B01J 2219/00315* (2013.01); *B01J 2219/00364* (2013.01); *B01J 2219/00644* (2013.01); *B01J 2219/00659* (2013.01); *B01J 2219/00664* (2013.01); *B01J 2219/00689* (2013.01); *B01J 2219/00691* (2013.01); *B01J 2219/00725* (2013.01); *B01J 2219/00743* (2013.01)

(58) Field of Classification Search
None
See application file for complete search history.

(56) References Cited

U.S. PATENT DOCUMENTS 7,709,256 B2 * 5/2010 Warren et al. ................. 435/372

OTHER PUBLICATIONS

Kuo et al. 2001. Ionically crosslinked alginate hydrogels as scaffolds for tissue engineering: Part 1. Structure, gelation rate and mechanical properties. Biomaterials, vol. 22, pp. 511-521.*
Sugiura et al (2005) Size control of calcium alginate beads containing living cells using micro-nozzle array. Biomaterials, vol. 22, pp. 511-521.*
Lee et al. Three-Dimensional Cell Culture Matrices: State of the Art. Tissue Engineering Part B: Reviews. (Mar. 2008), vol. 14, No. 1, pp. 61-86.*
Wang et al. 2005.Alginate encapsulation is a highly reproducible method for tumor cell implantation in dorsal skinfold chambers. Bio Techniques, vol. 39, No. 6, pp. 834-838.*
Mazia et al (1975).Adhesion of Cells to Surfaces Coated with Polylysine. Journal of Cell Biology, vol. 66, pp. 198-200.*
Paszek, M. J. et al. Tensional homeostasis and the malignant phenotype. Cancer Cell Sep. 2005, vol. 8, pp. 241-254.

* cited by examiner

*Primary Examiner* — Jon P Weber
*Assistant Examiner* — Kailash C Srivastava
(74) *Attorney, Agent, or Firm* — Harris Beach PLLC (57) ABSTRACT

A three-dimensional cell culture system is provided comprising one or more cell types of interest incorporated in a natural or synthetic hydrogel. An apparatus for high-throughput drug screening is also provided comprising a plurality of three-dimensional cell culture systems and a dispenser for placing at least one three-dimensional cell culture system into a predetermined well of a multiwell plate. A method for high-throughput drug screening is also provided that comprises providing a test agent, providing a three-dimensional cell culture system, determining a first cellular response of the cell of interest before culturing in the presence of the agent, culturing the cell of interest in the cell culture system in the presence of the agent, determining a second cellular response of the cell of interest after culturing in the presence of the agent, and comparing the first and second cellular responses.

25 Claims, 8 Drawing Sheets

PATHOLOGICALLY RELEVANT TUMOR MICROENVIRONMENTS FOR HIGH-THROUGHPUT DRUG SCREENING

CROSS-REFERENCE TO RELATED APPLICATIONS

This application claims priority to and the benefit of U.S. provisional patent application Ser. No. 61/084,328, entitled Pathologically Relevant Tumor Microenvironments for High-Throughput Drug Screening, filed Jul. 29, 2008, which is incorporated herein by reference in its entirety.

STATEMENT REGARDING FEDERALLY SPONSORED RESEARCH OR DEVELOPMENT

Not applicable

1. TECHNICAL FIELD

The present invention relates to three-dimensional cell culture systems.

The invention also relates to pathologically relevant tumor microenvironments for high-throughput drug screening. The invention further relates to three-dimensional culture systems that are biomimetic for tumors. The invention also relates to cell or tissue models. The invention further relates to heterotypic breast cancer models. The invention also relates to methods for high-throughput drug screening using three-dimensional cell culture systems.

2. BACKGROUND OF THE INVENTION

Microenvironmental conditions, in particular, three-dimensional cell-cell and cell-extracellular matrix interactions, are critically important in tumor induction and progression, and mediate the establishment of metastases at preferential target sites. Current strategies for preclinical testing of anti-cancer drugs, however, utilize two-dimensional cell culture in plastic dishes. This approach only marginally reflects the microenvironmental conditions present in tumors in vivo, and this shortcoming may contribute to the fact that many oncology compounds look promising in preclinical testing but fail in animal models and clinical trials.

Three-dimensional cell cultures to evaluate breast cancer progression are typically performed in Matrigel systems. This approach, however, is extremely time-consuming, exhibits limitations with regard to reproducibility due to batch to batch variations, and lacks the ability to recreate the elastic moduli typical of tumors in vivo.

There is therefore a need in the art for a three-dimensional, diversified tissue-engineered model system for elucidating microenvironmental events that currently impair the prognosis of cancer patients and to develop new drug screening systems for more effective treatment of cancer. There is also a need in the art for a three-dimensional cell culture system that has reproducible microenvironmental parameters and little or no batch-to-batch variations. There is a further need in the art for a three-dimensional cell culture system in which can be recreated the elastic moduli typical of tumors in vivo. There is also a need in the art for heterotypic cellular models for more efficient and biologically relevant testing of anti-cancer drug compounds in a high-throughput setting.

3. SUMMARY OF THE INVENTION

A three-dimensional cell culture system is provided. In one embodiment, the three-dimensional cell culture system comprises a cell of interest; and a natural or synthetic hydrogel incorporating (or combined with) the cell of interest. In another embodiment, the hydrogel incorporating the cell of interest can also encapsulate the cell of interest.

The three-dimensional cell culture system can be heterotypic or homotypic and the cultured cells can include, but are not limited to, cancer cells, tumor cells or normal stromal cells. The three-dimensional cell culture system can comprise a single cell (or cell type or cell line) or a plurality of cells of the same cell type (or cell line) or of different cell types (or lines).

In one embodiment, the three-dimensional culture system is biomimetic for tumors, especially human tumors. The three-dimensional cell culture system can be used for research or analytic purposes or for screening, e.g., drug screening. In one embodiment, the three-dimensional cell culture system can be used for high-throughput drug screening.

In one embodiment, the hydrogel is alginate-based.

In another embodiment, the hydrogel forms a roughly spherical bead. The bead can incorporate one or more cells or cell types.

In another embodiment, the diameter of the bead is 100-3000 µm.

In another embodiment, the cell culture system comprises a cell adhesion peptide modifying the hydrogel.

In another embodiment, the cell adhesion peptide is RGD, YIGSR [SEQ ID NO:1], or a derivative or modification thereof.

In another embodiment, the elastic modulus of the hydrogel is in the range of about $E=0.5$ kPa to $E=100$ kPa. In another embodiment, the value for the elastic modulus is about $E=0.5-5$ kPa, $E=5-10$ kPa, $E=10-20$ kPa, $E=20-60$ kPa, or $E=60-100$ kPa.

In another embodiment, the value for the elastic modulus is controlled by extent of crosslinking of the hydrogel.

In another embodiment, the hydrogel crosslinking is selected from the group consisting of chemically mediated crosslinking, ionically mediated crosslinking, thermally mediated crosslinking and photocrosslinking.

In another embodiment, the cell of interest is selected from the group consisting of a normal cell, benign cell, cancer cell, tumor cell, immortalized cell, genetically engineered cell, stem cell and patient-derived primary cell.

In another embodiment, the tumor cell or cancer cell is a breast tumor or cancer cell.

In another embodiment, the cell culture system comprises a second cell of interest of different cell type from the first cell of interest.

In another embodiment, the second cell of interest is associated with the hydrogel incorporating the cell of interest.

An apparatus for high-throughput drug screening is also provided. The apparatus can comprise: a plurality of three-dimensional cell culture systems, wherein each cell culture system comprises a cell of interest and a natural (e.g., alginate) or synthetic hydrogel incorporating the cell of interest; and a first dispenser for placing at least one three-dimensional cell culture system of the plurality into a pre-determined well of a multiwell plate.

In one embodiment, the apparatus comprises a movable stage for placing at least one three-dimensional cell culture system into the pre-determined well. In another embodiment, the movable stage is an X-Y transport stage.

In another embodiment, the apparatus comprises a second dispenser for placing a test agent into a pre-determined well of a multiwell plate.

In another embodiment, the first dispenser additionally dispenses a test agent into a pre-determined well of a multi-well plate.

In another embodiment, the first dispenser, the second dispenser or the movable stage can be computer-controlled.

In another embodiment, the first or second dispenser can be a syringe. The syringe can be controlled, e.g., by a computer-controlled syringe pump.

A method for screening a test agent is also provided. The method can comprise:

(a) providing a test agent;

(b) providing a three-dimensional cell culture system comprising a cell of interest and a natural or synthetic hydrogel incorporating the cell of interest;

(c) determining a first cellular response of the cell of interest before culturing in the presence of the agent;

(d) culturing the cell of interest in the cell culture system in the presence of the agent;

(e) determining a second cellular response of the cell of interest after culturing in the presence of the agent; and (f) comparing the first and second cellular responses.

In one embodiment, a plurality of three-dimensional cell culture systems is provided.

In another embodiment, the cells of interest in the plurality of three-dimensional cell culture systems comprise one or more cell types.

The cell(s) of interest can be selected from the group consisting of a normal cell, benign cell, cancer cell, tumor cell, immortalized cell, genetically engineered cell, stem cell and patient-derived primary cell.

In another embodiment, the agent is a drug, compound, biologically active agent or composition.

In another embodiment, the hydrogel comprises alginate.

In another embodiment, the first or second cellular response is cell growth, proliferation, differentiation or de-differentiation, inhibition of cell growth proliferation, differentiation or de-differentiation, cell death, cell survival, necrosis or inhibition of necrosis, cell-cell interaction(s), release of a cellular factor, transmitter or agent, release or uptake of an ion, change in cell adhesion, morphology or migration, or changes in an intracellular or extracellular signaling pathway.

In another embodiment, the cell of interest is selected from the group consisting of a normal cell, benign cell, cancer cell, tumor cell, immortalized cell, genetically engineered cell, stem cell and patient-derived primary cell.

In another embodiment, the tumor cell or cancer cell is a breast tumor or cancer cell.

In another embodiment, the cell culture system comprises a second cell of interest of different cell type from the first cell of interest.

In another embodiment, the culturing step comprises dynamically culturing the cell of interest in the cell culture system.

In another embodiment, the step of determining a second cellular response of the cell of interest after culturing in the presence of the agent comprises the step of releasing the cell of interest from the hydrogel prior to or after determining the second cellular response. In yet another embodiment, a genomic or proteomic analysis is performed on the released cell of interest.

A method for testing a response of a cell of interest to an microenvironmental condition of interest is also provided comprising:

(a) providing a three-dimensional cell culture system comprising the cell of interest and a natural or synthetic hydrogel incorporating the cell of interest;

(b) determining a first response of the cell of interest before culturing under the microenvironmental condition of interest;

(c) culturing the cell of interest in the cell culture system under the microenvironmental condition of interest;

(d) determining a second response of the cell of interest during, under, or after exposure to, the microenvironmental condition; and (e) comparing the first response and the second response of the cell of interest.

In one embodiment, a plurality of three-dimensional cell culture systems is provided.

In another embodiment, the cells of interest in the plurality of three-dimensional cell culture systems comprise one or more cell types.

The cell(s) of interest can be selected from the group consisting of a normal cell, benign cell, cancer cell, tumor cell, immortalized cell, genetically engineered cell, stem cell and patient-derived primary cell.

In another embodiment, the agent is a drug, compound, biologically active agent or composition.

In another embodiment, the hydrogel comprises alginate.

In another embodiment, the first or second cellular response is cell growth, proliferation, differentiation or de-differentiation, inhibition of cell growth proliferation, differentiation or de-differentiation, cell death, cell survival, necrosis or inhibition of necrosis, cell-cell interaction(s), release of a cellular factor, transmitter or agent, release or uptake of an ion, change in cell adhesion, morphology or migration, or changes in an intracellular or extracellular signaling pathway.

In another embodiment, the cell of interest is selected from the group consisting of a normal cell, benign cell, cancer cell, tumor cell, immortalized cell, genetically engineered cell, stem cell and patient-derived primary cell.

In another embodiment, the tumor cell or cancer cell is a breast tumor or cancer cell.

In another embodiment, the cell culture system comprises a second cell of interest of different cell type from the first cell of interest.

In another embodiment, the culturing step comprises dynamically culturing the cell of interest in the cell culture system.

In another embodiment, the step of determining a second cellular response of the cell of interest after culturing in the presence of the agent comprises the step of releasing the cell of interest from the hydrogel prior to or after determining the second cellular response. In yet another embodiment, a genomic or proteomic analysis is performed on the released cell of interest.

A method for making a three-dimensional cell culture system is also provided comprising:

(a) providing a natural or synthetic hydrogel solution;

(b) providing an isolated cell of interest;

(c) suspending the cell in the hydrogel solution; and (d) incorporating the cell in the hydrogel solution by crosslinking the hydrogel.

In one embodiment, the hydrogel solution is comprises alginate.

In another embodiment, the incorporation step comprises forming the hydrogel into a roughly spherical bead. The bead can incorporate one or more cells or cell types.

In another embodiment, the bead is 100-3000 μm in diameter.

In another embodiment, the crosslinking is chemically mediated, ionically mediated or thermally mediate crosslinking or photocrosslinking.

In another embodiment, the incorporation step can comprise extruding the suspended cell in the hydrogel solution into a crosslinking solution. In a specific embodiment, the hydrogel suspension is extruded into isotonic $CaCl_2$.

In another embodiment, the extruding step is performed under coaxial nitrogen flow.

In another embodiment, the hydrogel solution is modified with a cell adhesion peptide prior to incorporating the cell in the hydrogel solution.

In another embodiment, the hydrogel solution is 0.5-10% hydrogel.

In another embodiment, the cell density is $0-50 \cdot 10^6$ cells/mL hydrogel solution. In a specific embodiment, the hydrogel is alginate and the cell density is $0-50 \times 10^6$ cells/mL alginate hydrogel solution.

In another embodiment, the method comprises, after incorporating the cell, the step of associating the hydrogel incorporating the cell of interest with a second cell of interest of different cell type.

In another embodiment, two or more cells (or cell types) of interest can be incorporated or encapsulated.

In another embodiment, the method comprises pre-coating the hydrogel incorporating the cell of interest with a layer of poly-L-lysine prior to the step of associating the hydrogel with a second cell of interest of different cell type.

In another embodiment, the incorporated cell of interest is dynamically cultured.

In another embodiment, the cell of interest is selected from the group consisting of a normal cell, benign cell, cancer cell, tumor cell, immortalized cell, genetically engineered cell, stem cell and patient-derived primary cell.

In another embodiment, the tumor cell or cancer cell is a breast tumor or cancer cell.

In another embodiment, the cell culture system comprises a second cell of interest of different cell type from the first cell of interest.

In another embodiment, a pathologically relevant tumor microenvironment is provided. The pathologically relevant tumor microenvironment can be used for research or analytic purposes or for screening, e.g., drug screening.

In one embodiment, the pathologically relevant tumor microenvironment can be used for high-throughput drug screening.

Heterotypic or homotypic cell or tissue models are also provided. In one embodiment, the cell or tissue model is a heterotypic breast cancer model.

Methods for research, analysis or screening of test agents, e.g., high-throughput drug screening, using three-dimensional cell culture systems are also provided. In one embodiment, a method for high-throughput drug screening using pathologically relevant tumor microenvironments is provided.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIG. 3. (A) Cell viability of MDA-MB231 breast cancer cells encapsulated within RGD-modified alginate gels of varying stiffness as determined by live/dead staining and confocal analysis. (B) Coating of tumor beads with fluorescently labeled 3T3-L1 cells as visualized by confocal microscopy. 100-fold magnification.

FIG. 5. (A) IL-8 secretion of MDA-MB231 cells in 3-D matrices of different stiffness as measured by ELISA. (B) MDA-MB231 cell death in response to different doses of cisplatin and doxorubicin, which are widely-used chemotherapeutic drugs for the treatment of many types of cancer. Responsiveness to doxorubicin treatment in (two-dimensional) (2-D) versus three-dimensional (3-D) culture and as a function of mechanical stiffness of the utilized matrices (C).

FIG. 6. (A) 3T3-L1 proliferation and (B) VEGF secretion on soft vs. stiff RGD-alginate substrates. (C) Differentiation capacity of 3T3-L1 cells in 3-D RGD-alginate matrices of varying stiffness as determined by measurement of GPDH activity.

FIG. 7. (A) 3T3-L1 proliferation and (B) VEGF secretion in response to conditioned media collected from MCF-7 and MDA-MB231 cells. Unconditioned control media served as controls.

FIG. 8. (A) Brightfield (left) and fluorescence (right) photomicrographs of MDA-MB231 human breast cancer cells and 3T3-L1 mouse preadipocytes co-cultured in alginate beads. (B) When preadipocytes are cultured with the breast cancer cells, the breast cancer cells are more resistant to chemotherapeutic dosing. (C) The breast tumor cells upregulate secretion of the pro-angiogenic factor VEGF, when co-cultured with the preadipocytes. (D) The function of the preadipocytes within the tumor microenvironment is also altered in that their ability to differentiate is decreased in both 3D co-culture with MDA-MB231 breast cancer cells and (E) 2D culture in media conditioned by MCF-7 or MDA-MB231 breast cancer cells as measured by GPDH activity.

5. DETAILED DESCRIPTION OF THE INVENTION

A three-dimensional (3-D) cell culture system based on the incorporation of cells of interest in natural or synthetic hydrogels is provided. In one embodiment, the hydrogel is an alginate hydrogel (i.e., comprises alginate or is alginate-based). The three-dimensional cell culture system can be heterotypic or homotypic and the cultured cells can include, but are not limited to, cancer cells, tumor cells or normal cells. When used for culturing two or more types of heterotypic cells, the three-dimensional culture system can be used, for example, to study the cell-cell interactions between different types of cells or for high-throughput drug screening in a heterotypic cell environment. In one embodiment, tissue engineering strategies can be applied to recreate typical cell-microenvironment interactions (e.g., 3-D cell-cell and cell-extracellular matrix interactions, mechanical stiffness, soluble factor presentation).

A pathologically relevant tumor microenvironment is also provided. The pathologically relevant tumor microenvironment can be used for research or analytic purposes or for screening, e.g., drug screening. In one embodiment, the pathologically relevant tumor microenvironment can be used for high-throughput drug screening.

In another embodiment, heterotypic breast cancer models are provided for more efficient and biologically relevant testing of anticancer drug compounds in a high-throughput setting. In one embodiment, tissue engineering strategies can be applied to develop biomimetic human tumors that recreate typical cell-microenvironment interactions (e.g., 3-D cell-cell and cell-extracellular matrix interactions, mechanical stiffness, soluble factor presentation) at the mammary tumor/adipose tissue interface. These 3-D culture systems can be used to study the physicochemical crosstalk between tumor cells (e.g. breast cancer cells) and normal cells (e.g. adipose tissue-derived cells) and assess the importance of this mechanism on cancer progression and, conversely, on responsiveness to anti-cancer therapy.

Engineered human tumor models (or "biomimetic tumors") can be up-scaled and validated, using standard methods, for high-throughput screening of anti-cancer drugs. By mimicking typical microenvironmental conditions of human tumors, the provided technology overcomes the well-known limitations associated with conventional cell culture approaches and non-human animal models (although in certain embodiments, animal models or tumors can be used as well).

The three-dimensional cell culture systems provided by the invention can be used to dramatically reduce drug development costs for the pharmaceutical industry (up to $14 million for each new drug in the pipeline, based on an assumed 10% improvement).

For clarity of disclosure, and not by way of limitation, the detailed description of the invention is divided into the subsections set forth below.

5.1. Three-Dimensional Cell Culture System

A three-dimensional cell culture system is provided. In one embodiment, the three-dimensional cell culture system comprises a cell of interest and a natural or synthetic hydrogel incorporating the cell of interest. In other embodiments, one or more cells (or cell types) of interest can be incorporated.

The three-dimensional cell culture system can comprise a single cell (or cell type) or a plurality of cells of the same cell type or of different cell types.

In one embodiment, the incorporating hydrogel forms a roughly spherical bead. The bead can incorporate one or more cells or cell types. In another embodiment, the diameter of the bead is 100-3000 μm.

Any suitable hydrogel known in the art can be employed in the cell culture system, as long as its stiffness can be manipulated to produce a suitable or appropriate stiffness (or range of stiffnesses). Such suitability can be easily determined by one of skill in the art. In a specific embodiment, an alginate hydrogel (i.e., a hydrogel comprising hydrogel or alginate-based hydrogel) is used.

At least one cell is incorporated in the hydrogel or cell culture system. In a preferred embodiment, a plurality of cells is incorporated in the hydrogel solution or in the cell culture system. In another preferred embodiment, the cell culture system can comprise a plurality of cells of interest that can be of one cell type (or cell line) or of multiple cell types (or lines).

Figure 1:
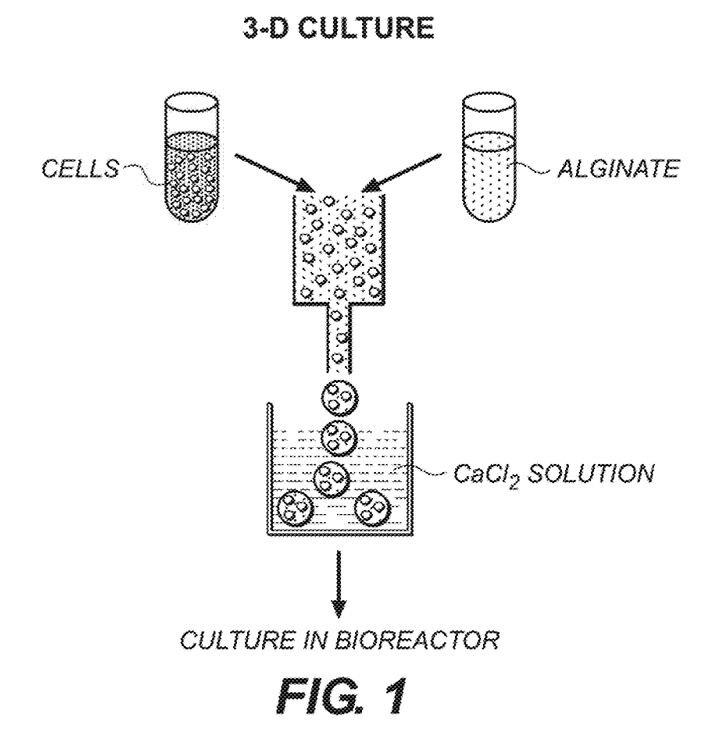
FIG. 1. One embodiment of the three-dimensional (3-D) cell culture system. Tumor cells in the presence or absence of other cell types are incorporated and cultured in three-dimensional alginate-based matrices of differential stiffness.

One embodiment of the three-dimensional (3-D) cell culture system is shown in FIG. 1. Tumor cells are incorporated in the absence or presence of other cells and cultured in three-dimensional alginate-based matrices of differential stiffness. In one embodiment, the stiffness ranges from 1 to 60 kPa. In another embodiment, stiffness is about 1-5 kPa (e.g., normal tissue exhibits stiffnesses of up to 1 kPa). In another embodiment, the stiffness ranges from about tumors 5-10 kPa (e.g., 5 kPa for "soft" tumors, 10 kPa for "hard" tumors).

Figure 2:
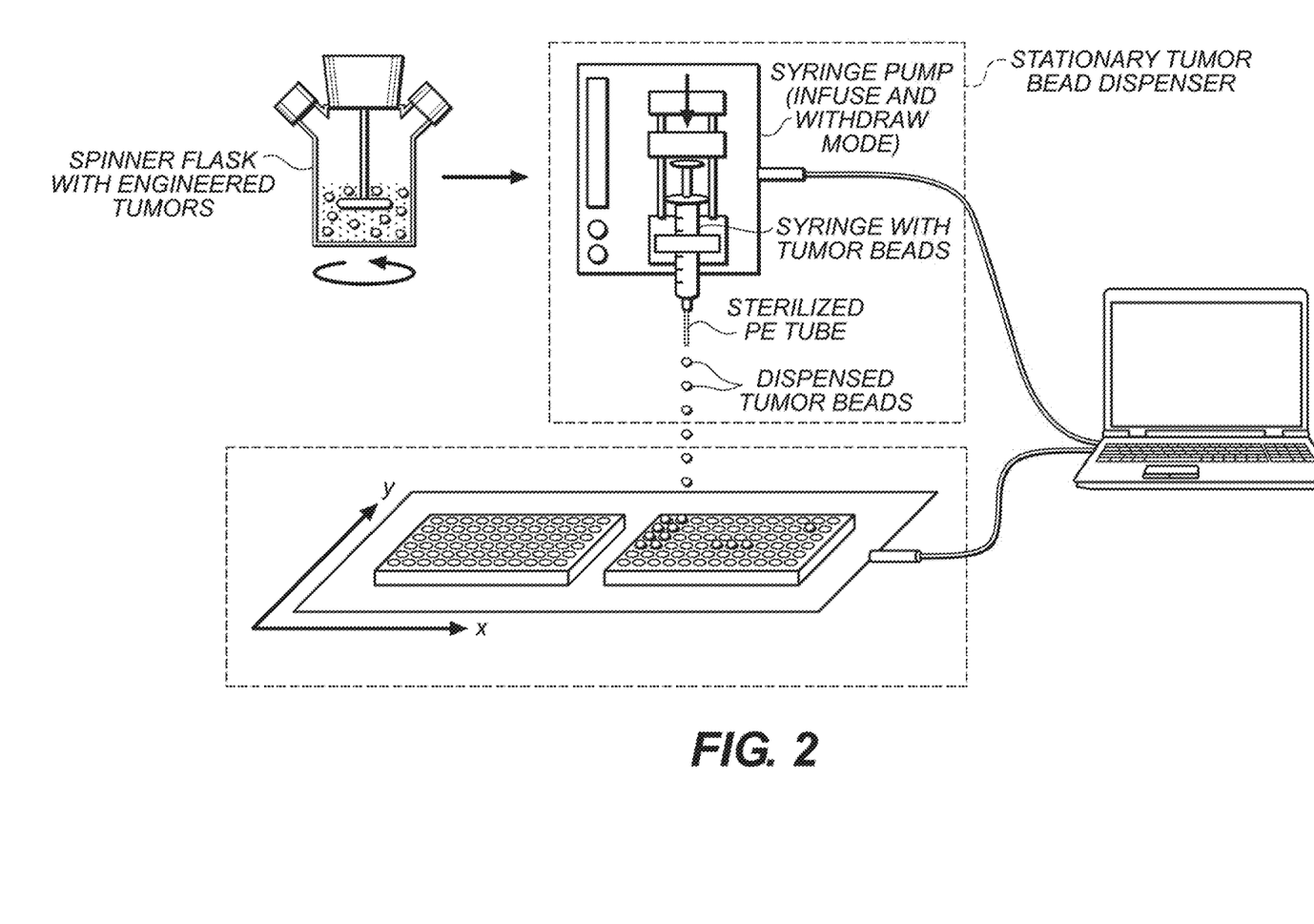
FIG. 2. Another embodiment of the three-dimensional cell culture system, being used for high-throughput screening of chemotherapeutic drugs in a pathologically more relevant setting. Heterotypic 3-D tumor models can be pre-fabricated under dynamic culture conditions in a spinner flask and then loaded into a stationary tumor bead dispenser. Using a computer-controlled syringe pump in combination with a computer-controlled movable stage, tumor beads can be dispensed at a pre-defined rate into pre-defined wells.

Another embodiment of the three-dimensional cell culture system is shown in FIG. 2. The three-dimensional cell culture system can be used for high-throughput screening of chemotherapeutic drugs in a pathologically more relevant setting. Heterotypic 3-D tumor models can be pre-fabricated under dynamic culture conditions in a spinner flask and then loaded into a stationary tumor bead dispenser. Using a computer-controlled syringe pump in combination with a computer-controlled movable stage, tumor beads can be dispensed at a pre-defined rate into pre-defined wells.

In one embodiment, standard tissue engineering strategies known in the art are used to create a biomimetic human tumor in the three-dimensional cell culture system that recreates typical cell-microenvironment interactions (i.e., 3-D cell-cell and cell-extracellular matrix interactions, mechanical stiffness, soluble factor presentation) at the mammary tumor/adipose tissue interface.

The 3-D culture systems can be used to study the cell-cell interactions or physicochemical communication between cancer cells (e.g. breast cancer cells) and normal stroma cells (e.g. adipose tissue-derived cells). These mechanisms can be evaluated with respect to their role in cancer progression or on tumor cell responsiveness to anti-cancer therapy.

In one embodiment, the 3-D culture systems can be human tumor models (biomimetic tumors) that are up-scaled and validated using methods known in the art for use in high-throughput screening of anti-cancer drugs. By mimicking typical microenvironmental conditions of human tumors, the 3-D culture system has many advantages over conventional cell culture approaches, overcomes the limitations associated with non-human animal models and reduces drug development costs. The 3-D culture systems can therefore be used to enhance understanding of cancer biology and development of drug resistance.

Three-dimensional cell culture systems are provided for the study of disease, disorders and other conditions that affect cell growth, proliferation, differentiation or de-differentiation, inhibition of cell growth proliferation, differentiation or de-differentiation, cell death, cell survival (e.g., anti-apoptotic signaling), necrosis or inhibition of necrosis, release of soluble signaling factors (e.g., hormones, growth factors, cytokines), transmitter (e.g., a neurotransmitter) or other morphogens (e.g., protease), release or uptake of an ion (e.g., Ca, Na, K), change in cell adhesion, morphology, and migration, and the associated intracellular and extracellular signaling pathways.

The cultured cells can be homotypic or heterotypic. Two or more heterotypic cells or cell-types can be cultured together.

In one embodiment, cancer cell growth and progression can be studied using the 3-D cell culture systems. In another embodiment, two or more cell types contributing to tumor development in vivo can be cultured together.

In another embodiment, the three-dimensional cell culture system comprises synthetic versions of biomaterials that have mechanical stiffness (i.e., elastic moduli) that can be readily adjusted from ranges occurring in normal tissues (up to 1 kPa) to values measured for human tumor tissues (~5-15 kPa).

The elastic modulus of the natural or synthetic hydrogel can be in the range of about $E=0.5$ kPa to $E=100$ kPa. In another embodiment, the value for the elastic modulus is about E=0.5-5 kPa, E=5-10 kPa, E=10-20 kPa, E=20-60 kPa, or E=60-100 kPa.

In some embodiments, instead of using a single cell type, the 3-D culture system can combine two or more types of normal or pathologic cell types contributing to a disease or disorder in vivo.

In one embodiment, breast cancer cells and adipose tissue-derived cells can be cultured together as a model for breast cancer in situ. Adipose tissue-derived cells are situated in the immediate environment of mammary tumors and have been previously shown to be involved in breast cancer progression. In a specific embodiment, an alginate-based three-dimensional cell co-culture system is used to study the contribution of adipose tissue-derived cells to reduced drug responsiveness and enhanced malignant potential of breast cancer cells (see FIG. 8).

In another embodiment, the heterotypic (2 or more cell type) culture systems are utilized in a high-throughput manner rather than in individualized culture, ultimately enhancing the industrial applicability and efficacy of the 3-D cell culture system.

Although certain embodiments of the 3-D cell culture system can be based on the importance of stromal cell compartments in breast cancer, the 3-D cell culture system is readily applicable to other types of cancer or cellular disorders, and, hence, drug testing can be conducted for these conditions as well using the 3-D cell culture system.

In one embodiment of the 3-D culture system, values for elastic moduli in normal tissue and at a tumor or cancer interface with neighboring or surrounding non-tumor or non-cancer cells are recreated using a hydrogel, e.g., an alginate-based hydrogel. In specific embodiments, the values for the elastic modulus is in the range of about E=0.5 kPa to E=100 kPa. In other specific embodiments, the value for the elastic modulus is about E=0.5-5 kPa, E=5-10 kPa, E=10-20 kPa, E=20-60 kPa, or E=60-100 kPa.

In another embodiment, the hydrogel (e.g., an alginate hydrogel) is modified with one or more cell adhesion peptides (or types of cell adhesion peptides) e.g., RGD, YIGSR [SEQ ID NO: 1], or a derivative or modification thereof. Such peptides (and their derivatives or modification) are well known in the art and commercially available. Arginylglycy-laspartic acid (RGD), more commonly known as arginine-glycine-aspartic acid (Arg-Gly-Asp) is a tripeptide that is a versatile cell recognition site for numerous adhesive proteins (e.g., fibronectin) and involved in cell binding. The RGD tri-peptide, as well as modifications of this peptide (e.g., YIGSR [SEQ ID NO: 1], a peptide sequence derived from the extracellular matrix protein laminin), are well known in the art and commercially available (e.g., from Peptides International, Louisville, Ky.). Methods for modifying hydrogels by linking them to bioactive compounds such as cell adhesion molecules are well known in the art (see, e.g., U.S. Pat. No. 7,186,413, Hydrogels and water soluble polymeric carriers for drug delivery, by Bouhadir et al., Mar. 6, 2007).

In a specific embodiment of the 3-D culture system, values for elastic moduli in normal mammary tissue and at the mammary tumor/adipose tissue interface are recreated using alginate-based hydrogels modified with cell adhesion peptides (e.g., RGD or YIGSR [SEQ ID NO: 1]). For example, elastic moduli can be adjusted to, e.g., E=I, 5, 20, and 60 kPa by the extent of crosslinking of the utilized alginate, while RGD-modification provides for cellular interactions with the material. This embodiment can provide for constant concentration of cell adhesion sites throughout all materials of the 3-D culture, allowing for direct correlation of cell behavior with changes in matrix stiffness.

Crosslinking of hydrogel can be accomplished by any means known in the art, for example, by chemically mediated, ionically mediated or thermally mediated crosslinking, or by photocrosslinking.

5.2 Methods for Making Three-Dimensional Culture Systems

A method for making a three-dimensional cell culture system is provided comprising: providing a natural or synthetic hydrogel solution; providing an isolated cell of interest; suspending the cell in the hydrogel solution; and incorporating the cell in the hydrogel solution by crosslinking the hydrogel.

In one embodiment, the hydrogel solution comprises alginate. In another embodiment, incorporation of the cell in the hydrogel is accomplished by extruding the cell suspended in the hydrogel solution into a crosslinking solution. In another embodiment, the hydrogel is formed into a roughly spherical bead during the incorporation step.

In another embodiment, the bead is 10-1000 μm in diameter. In another embodiment, the bead is 100-3000 μm in diameter.

Crosslinking can be by any means known in the art, e.g., chemically or ionically mediated crosslinking, thermal crosslinking or photocrosslinking.

In another embodiment, the hydrogel can be ionically crosslinked by extruding the suspension into a solution comprising calcium, e.g. isotonic $CaCl_2$, which initiates the crosslinking.

In another embodiment, the extruding step is performed under coaxial nitrogen flow.

In another embodiment, the hydrogel solution can be modified with a cell adhesion peptide prior to incorporating the cell in the hydrogel.

In another embodiment, the hydrogel solution is 0.5-10% hydrogel. In a specific embodiment, hydrogel solution is 0.5-10% alginate hydrogel.

In another embodiment, the cell density is $0-50 \times 10^6$ cells/mL of hydrogel solution. In a specific embodiment, the cell density is $0-50 \times 10^6$ cells/mL of alginate-based hydrogel solution.

In another embodiment, the method comprises, after the step of incorporating the cell of interest, the step of associating the hydrogel incorporating the cell of interest with a second cell of interest of different cell type. In one embodiment, one or more cell types can be dispersed or incorporated within the hydrogel. In another embodiment one or more cell types can be dispersed or incorporated within the hydrogel and another cell type (or two or more cell types) can be associated with, bound to, disposed on, or coated on the surface of the hydrogel. Cells can be attached to the hydrogel via any mechanism known in the art. Other combinations of cell types dispersed within the hydrogel and/or on the surface of the hydrogel will be readily apparent to one of skill in the art.

Figure 3A:
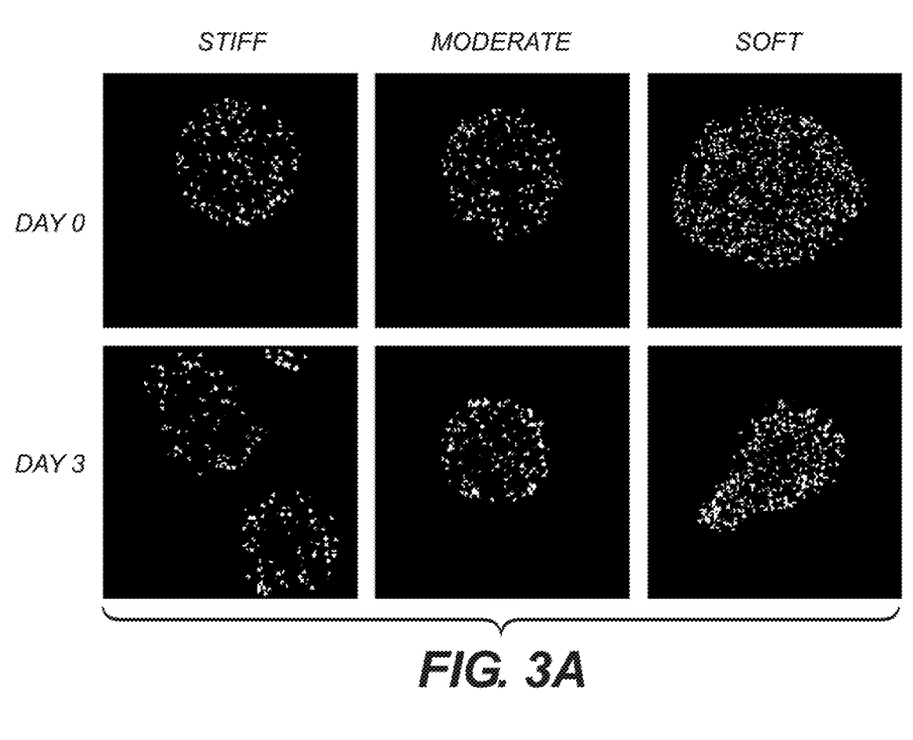
Figure 3B:
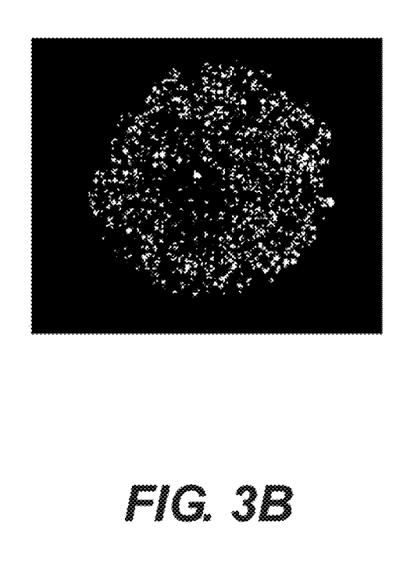

In another embodiment, the method comprises pre-coating the hydrogel incorporating the cell of interest with a layer of poly-L-lysine prior to the coating step (FIG. 3B).

In another embodiment, the method comprises dynamically culturing the incorporated cell of interest.

For example, to engineer a biomimetic tumor, tumor cells of interest are dispersed in cell adhesion peptide-modified alginate solutions (0.5-3%) at a desired density of cells/mL alginate to yield homogenous encapsulation (or incorporation) of cells throughout the matrix. Such density can be easily determined by one of skill in the art. This suspension is then extruded under a coaxial nitrogen flow into a crosslinking solution, e.g., isotonic $CaCl_2$ solution, using an encapsulation unit, whereby the size of the beads can be readily modulated by varying the rate of nitrogen flow. Encapsulation apparatuses, as well as crosslinking solutions, flow rates and other encapsulation parameters are well known in the art.

In a specific embodiment, to engineer mammary tumors breast cancer cells are dispersed in RGD-modified alginate solutions (2%) at a density of $20 \times 10^6$ cells/mL alginate. This suspension is then extruded under a coaxial nitrogen flow into isotonic $CaCl_2$ solutions using a self-made (or commercially available, e.g., from Nisco) encapsulation unit at a speed of 1 mL/min, whereby the size of the beads can be readily modulated by varying the rate of nitrogen flow (FIG. 1).

In one embodiment, central hypoxia, a key characteristic of cancer contributing to malignancy and development of drug resistance can be recreated in the 3-D culture system. Extrusion parameters can be set to yield 3-D culture systems (biomimetic tumors) of >400 µm in diameter as the diffusion limit for oxygen in in situ tumors averages 100-200 µm.

Heterotypic tumor or cancer models can be formed by subsequent coating or associating of the 3-D culture system with another cell type using methods known in the art. Heterotypic breast cancer models can be formed, for example, by subsequent associating or coating with adipose-tissue derived progenitor cells under dynamic conditions in spinner flasks. Cell adhesion onto beads may be enhanced by pre-coating with a monomolecular layer of poly-L-lysine (FIG. 3B). The heterotypic tumors can be dynamically cultured in spinner flasks under art known culture conditions, e.g., for 0, 5, 10, and 15 days and utilized for basic research and analysis of drug responsiveness as disclosed hereinbelow.

5.3 Methods for Screening Test Agents and for Testing Microenvironmental Conditions The invention provides a method for screening a test agent comprising:

(a) providing a test agent;

(b) providing a three-dimensional cell culture system comprising a cell of interest and a natural or synthetic hydrogel (e.g., an alginate-based hydrogel) incorporating the cell;

(c) determining a first cellular response of the cell of interest before culturing in the presence of the agent;

(d) culturing the cell of interest in the cell culture system in the presence of the agent;

(e) determining a second cellular response of the cell of interest after culturing in the presence of the agent; and (f) comparing the first and second cellular responses.

In one embodiment, the agent is a drug, compound, biologically active agent or composition.

In another embodiment, the first or second cellular response is cell growth, proliferation, differentiation or de-differentiation, inhibition of cell growth proliferation, differentiation or de-differentiation, cell death, cell survival, necrosis or inhibition of necrosis, cell-cell interaction(s), release of a cellular factor, transmitter or agent, release or uptake of an ion, or change in cell adhesion, morphology, and migration, and the related intra- and extracellular signaling.

In another embodiment, the cell of interest is selected from the group consisting of a normal cell, benign cell, cancer cell, tumor cell, immortalized cell, genetically engineered cell, stem cell and patient-derived primary cell.

In another embodiment, the tumor cell or cancer cell is a breast tumor or cancer cell.

In another embodiment, the cell culture system comprises a second cell of interest of different cell type from the first cell of interest. In another embodiment, the cell culture system can comprise a plurality of cells of interest that can be of one cell type (or line) or of multiple cell types (or lines).

In another embodiment, the culturing step comprises dynamically culturing the cell of interest in the cell culture system.

In another embodiment, determining a second cellular response of the cell of interest after culturing in the presence of the agent comprises the step of releasing the cell of interest from the hydrogel prior to or after determining the second cellular response. In another embodiment, this determining step comprises performing genomic or proteomic analysis on the released cell of interest.

In another embodiment, a method is also provided for testing a response of a cell of interest to an microenvironmental condition of interest comprising:

(a) providing a three-dimensional cell culture system comprising the cell of interest and a natural or synthetic hydrogel (e.g., alginate hydrogel) incorporating the cell of interest;

(b) determining a first response of the cell of interest before culturing under the microenvironmental condition of interest;

(c) culturing the cell of interest in the cell culture system under the microenvironmental condition of interest;

(d) determining a second response of the cell of interest during, under, or after exposure to, the microenvironmental condition; and (e) comparing the first response and the second response of the cell of interest.

The microenvironmental condition can be, e.g., 3-D cell-cell and cell-extracellular matrix interactions, mechanical stiffness, soluble factor presentation, oxygen level, pH, presence or absence of biologically active agent or any other cell microenvironmental condition known in the art.

The first or second cellular response can be (as described above) cell growth, proliferation, differentiation or de-differentiation, inhibition of cell growth proliferation, differentiation or de-differentiation, cell death, cell survival, necrosis or inhibition of necrosis, cell-cell interaction(s), release of a cellular factor, transmitter or agent, release or uptake of an ion, or change in cell adhesion, morphology, and migration, and the related intra- and extracellular signaling.

The cell of interest can be selected from the group consisting of a normal cell, benign cell, cancer cell, tumor cell, immortalized cell, genetically engineered cell, stem cell and patient-derived primary cell. The tumor cell or cancer cell can be a breast tumor or cancer cell.

The cell culture system can comprise (as described above) a second cell of interest (or plurality of cells) of different cell type from the first cell of interest. The cell culture system can comprise a plurality of cells of interest that can be of one cell type (or line) or of multiple cell types (or lines).

In another embodiment, the culturing step comprises dynamically culturing the cell of interest in the cell culture system.

In another embodiment, determining a second cellular response of the cell of interest after culturing in the presence of the agent comprises the step of releasing the cell of interest from the hydrogel prior to or after determining the second cellular response. In another embodiment, this determining step comprises performing genomic or proteomic analysis on the released cell of interest.

5.4 Apparatus for Efficient or High-Throughput Screening

The above-described methods can be used as the basis for apparatuses (or platforms) for efficient screening of agents (e.g., drug, compound, biologically active agent or composition) in a high-throughput manner for operation under sterile conditions. Such apparatuses can be automated or computer-controlled using methods well known in the art.

In one embodiment an apparatus for high-throughput drug screening is provided. The apparatus can comprise: a plurality of three-dimensional cell culture systems, wherein each cell culture system comprises a cell of interest and a natural (e.g., alginate) or synthetic hydrogel incorporating the cell of interest; and a first dispenser for placing at least one three-dimensional cell culture system of the plurality into a pre-determined well of a multiwell plate.

In one embodiment, the apparatus comprises a movable stage for placing at least one three-dimensional cell culture system into the pre-determined well. In another embodiment, the movable stage is an X-Y transport stage.

In another embodiment, the apparatus comprises a second dispenser for placing a test agent into a pre-determined well of a multiwell plate.

In another embodiment, the first dispenser additionally dispenses a test agent into a pre-determined well of a multiwell plate.

In another embodiment, the first dispenser, the second dispenser or the movable stage can be computer-controlled.

In another embodiment, the first or second dispenser can be a syringe. The syringe can be controlled, e.g., by a computer-controlled syringe pump.

One embodiment of this apparatus comprises a stationary module that comprises a dispenser designed to place biomimetic tumors into multiwell (e.g., 96-well) plates, while a second module can be a multi-station, computer-controlled stage that allows for customized seeding of tumors into pre-determined wells by a XY transport design (FIG. 2).

In another embodiment, heterotypic tumors (e.g., 0.5 mm diameter) can be pre-fabricated in spinner flasks as described above and manually loaded into a syringe that is connected to an ethylene oxide gas-sterilized PE tube (e.g., 0.76 mm inner diameter×1.22 mm outer diameter). Using a computer-controlled syringe pump in combination with the computer-controlled movable stage, tumor beads can be dispensed at a pre-defined rate into pre-defined wells. The same experimental set-up can be utilized to dispense cell culture media containing different types, concentrations, and combinations of chemotherapeutic drugs into the tumor containing wells.

Plates can be dynamically cultured on an orbital shaker and media changes can be performed exploring the same platform, but using the 'withdraw' mode of the syringe pump. High-throughput analysis of tumor cell proliferation and death in response to chemotherapy can then be conducted. Furthermore, cells contained in tumor beads can be readily utilized for genomic or proteomic analysis following release from alginate by brief incubation in, e.g., 50 mM EDTA/PBS.

Although the above-described embodiment provides a heterotypic breast cancer model to evaluate the importance of stromal cell compartments in breast cancer, it is readily applicable to any other type of cell or tissue, including but not limited to normal cells, benign cells, cancer cells, tumor cells, immortalized cells, genetically engineered cells, stem cell and patient-derived primary cells, and, hence, drug testing for these conditions as well. In another embodiment, the 3-D culture system can be used to grow cells for investigatory purposes such as testing wild-type or normal cells for their responses to exposure to an agent (e.g., drug, compound, biologically active agent or composition) or to a microenvironmental condition of interest.

Furthermore, the 3-D culture systems can be developed from other biocompatible polymers that allow for cell adhesion and can be modified with regard to their mechanical stiffness. For example, in another embodiment, photo-crosslinked RGD-modified alginate gels can be used.

In other embodiments, the invention provides culture systems for basic research of cancer and testing of anti-cancer drug candidates in the pharmaceutical industry.

The following example is offered by way of illustration and not by way of limitation.

6. EXAMPLE

6.1 Pathologically Relevant Three-Dimensional Tumor Microenvironments

This example demonstrates the development of 3-D cell and disease models that more closely mimic the signaling present in tumors in vivo. These biomimetic systems are used for drug testing under more realistic culture conditions. Biomimetic 3-D tumors were developed and characterized. Differential interactions were examined between different cell types as regulated by mechanical stiffness and soluble factors in 3-D cultures to regulate tumor malignancy and responsiveness to chemotherapy. The cells studied were MDA-MB231 breast cancer cells and adipose-tissue derived cells as a biomimetic for breast cancer.

MDA-MB231 human breast cancer cells were incorporated within RGD-modified alginate gels of varying stiffness. Using live/dead staining of these cells by calcein/propidium iodide, the cells were observed to maintain cellular viability during the encapsulation procedure and following dynamic 3-D culture (FIG. 3A). Subsequently, these biomimetic tumors were coated with adipose-tissue derived cells. 3T3-L1 mouse preadipocytes were used as an inexpensive model cell line.

3T3-L1 preadipocytes were pre-labeled with a fluorescent membrane dye to distinguish them from the incorporated MDA-MB213 cells. 3T3-L1 cells did not adhere to untreated tumor beads. Pre-coating them with 0.1 mg/mL poly-L-lysine, however, allowed them to attach to the outside of the beads (FIG. 3B).

In addition, 3-D studies using 3T3-L1 cells pre-encapsulated within RGD-modified alginate gels allowed assessment of the differences in tumor malignancy and drug responsiveness as a function of direct effects (e.g., cell-cell interactions) versus indirect effects (e.g., via soluble factors) between breast cancer cells and adipose tissue-derived cells.

Figure 4:
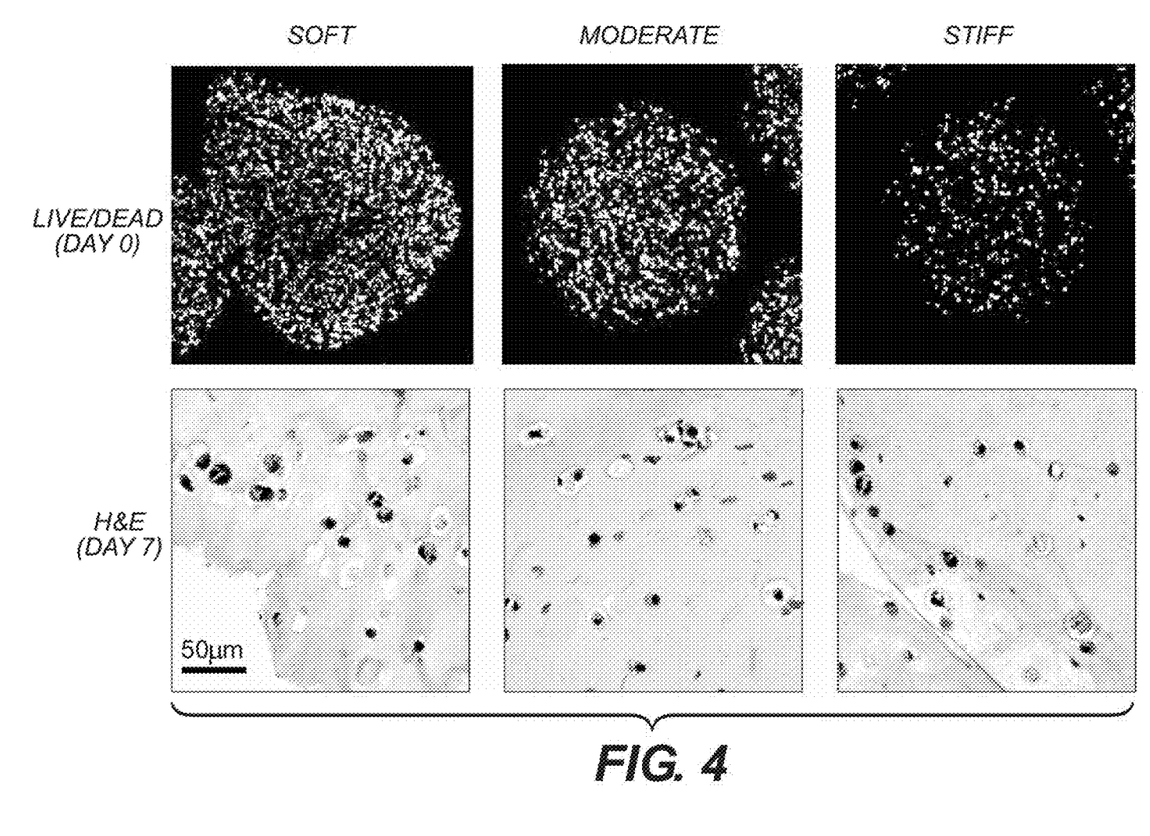
FIG. 4: 3T3-L1 encapsulated within RGD-modified alginate as visualized by live/dead assay and confocal analysis on day 0 (100-fold magnification), and H&E staining of histological cross-sections after 7 days of dynamic culture.

Similar to the above-described data, 3T3-L1 maintained their viability during the encapsulation process and following long-term culture under dynamic conditions (FIG. 4). These results were independent of the mechanical properties of the gel matrix utilized.

Figure 5A:
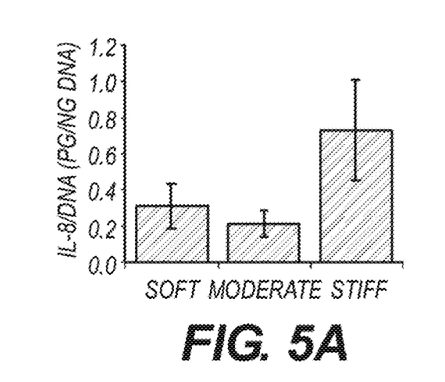

To examine tumor malignancy and efficacy of anti-cancer drugs in response to enhanced mechanical stiffness, MDA-MB231 were incorporated in 3-D RGD-modified alginate cultures and were evaluated for proliferation, secretion of a molecular marker of enhanced malignancy (i.e., interleukin-8 (IL-8)), and drug responsiveness. Analysis of conditioned media via ELISA revealed that IL-8 secretion was significantly enhanced by increased matrix stiffness (FIG. 5A).

For the drug testing studies, different doses of two frequently utilized chemotherapeutic drugs were first evaluated with regard to their ability to reduce breast cancer cell viability in conventional 2-D culture.

Figure 5B:
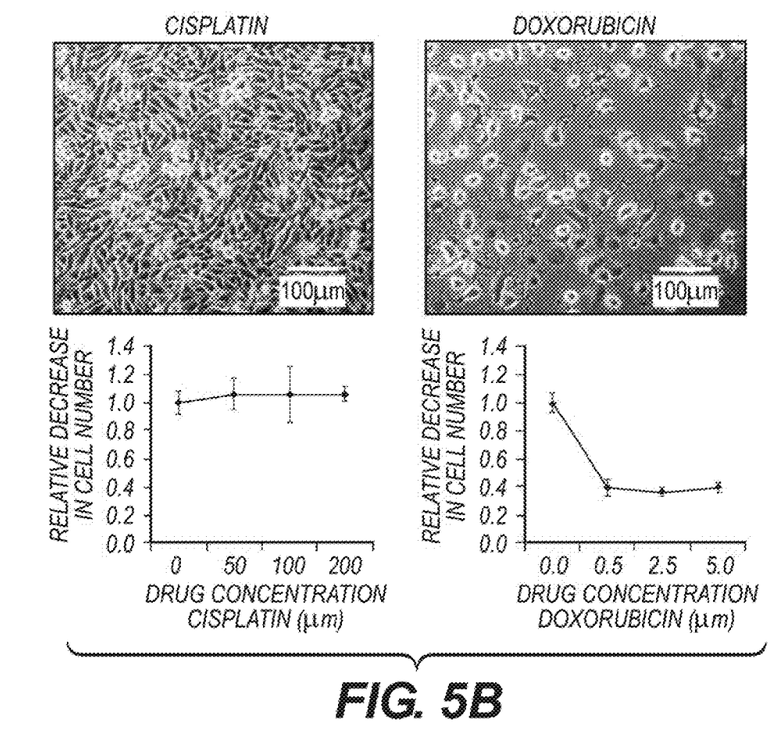

Data (FIG. 5B, left panel) indicated that high doses of cisplatin did not alter MDA-MB231 viability in 2-D culture, whereas 0.5 µM doxorubicin efficiently reduced the number of viable tumor cells in 2-D culture (FIG. 5B, right panel).

Figure 5C:
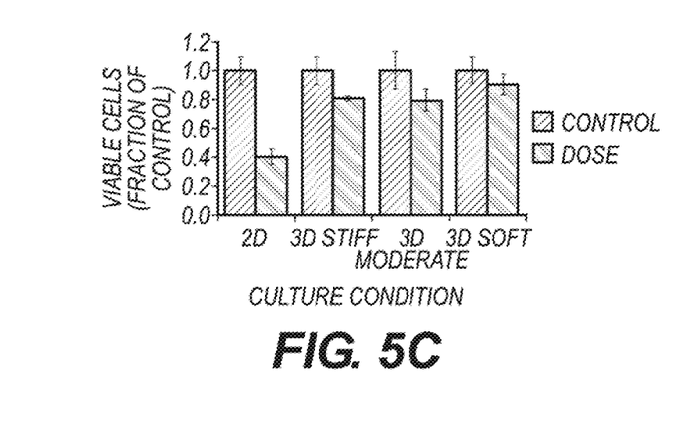

Consequently, all subsequent drug testing studies were performed with doxorubicin. Application of doxorubicin to both 2-D monolayer cultures and 3-D cultures within RGD-modified alginate gels subsequently elucidated that 3-D microenvironmental conditions dramatically-reduce the efficacy of doxorubicin treatment relative to 2-D conditions (FIG. 5C).

Figure 6A:
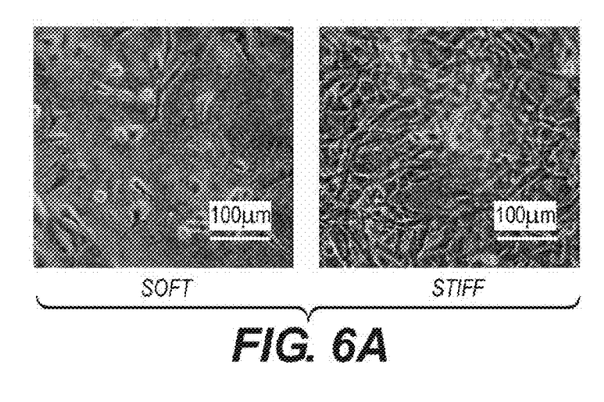
Figure 6B:
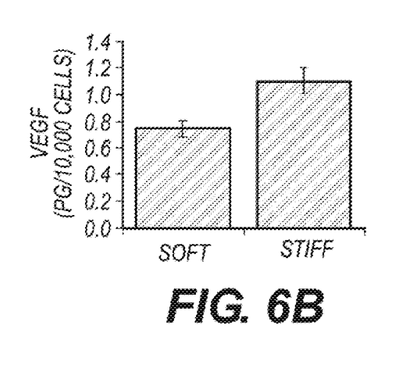
Figure 6C:
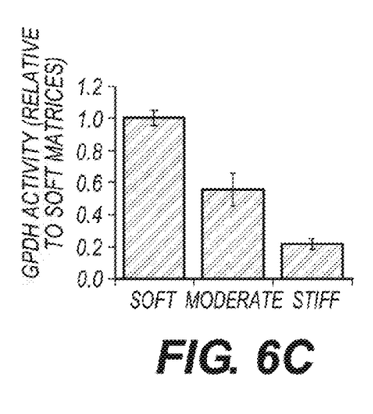

To examine whether adipose tissue-derived cells differentially respond to altered mechanical cues within the breast cancer microenvironment, the proliferation, differentiation, and secretion behaviors of adipose tissue progenitor cells were evaluated in response to altered RGD-alginate matrix stiffness. Soft (~5 kPa) and stiff (~10 kPa) matrices were fabricated from RGD-modified alginate and seeded with 3T3-L1 cells. Cells proliferated faster on stiff matrices relative to soft ones (FIG. 6A) and secreted enhanced concentrations of vascular endothelial growth factor (VEGF) (FIG. 6B), a morphogen that directly and indirectly enhances tumor malignancy by altering breast cancer cell functions and increasing tumor vascularization, respectively. FIG. 6C shows the differentiation capacity of 3T3-L1 cells in 3-D RGD-alginate matrices of varying stiffness as determined by measurement of GPDH activity.

Additionally, 3T3-L1 cells were incorporated within 3-D matrices of varying stiffness and their rate of autonomous (i.e., in the absence of hormonal induction) differentiation capacity was determined via analysis of GPDH activity, a key enzyme involved in lipid biosynthesis. Cells within stiff matrices exhibited significantly reduced activities of GPDH, suggesting that they maintained their undifferentiated status in breast cancer microenvironments, whereas they are more likely to undergo adipogenic differentiation in normal mammary tissue microenvironments.

To further determine whether tumor cell-derived soluble factors alter adipose tissue progenitor cell behavior, 3T3-L1 cells were cultured in tumor conditioned media. Their proliferation and secretion of the pro-malignant factor VEGF was determined. Media from both MCF-7 and MDA-MB231 breast cancer cells were collected, normalized to the same cell number and their effect was compared with those mediated by unconditioned control media.

Figure 7A:
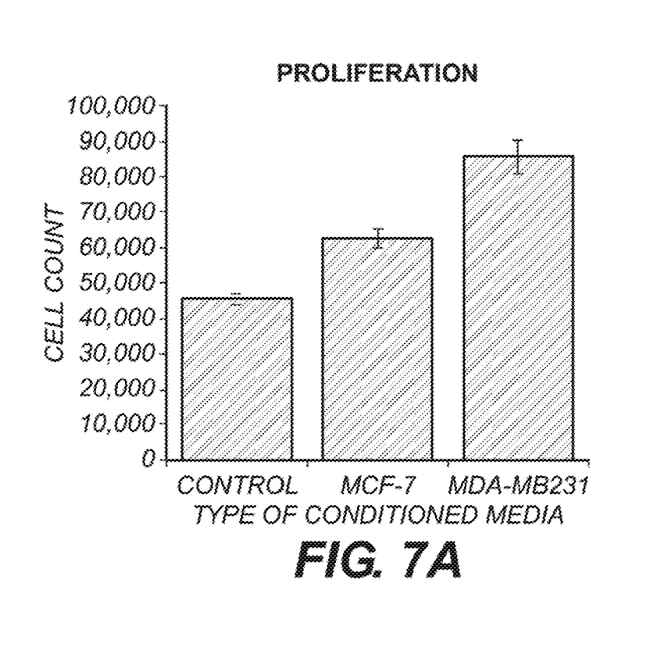
Figure 7B:
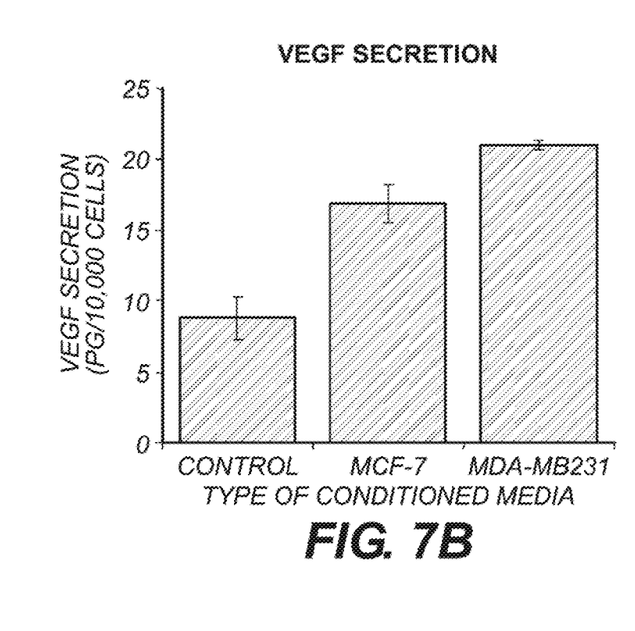

MCF-7 and MDA-MB231 breast cancer cells represent cell models of less and more malignant stages of breast cancer, respectively, and allowed evaluation of adipose tissue progenitor cell behavior as a function of tumor malignancy. Tumor conditioned media significantly increased 3T3-L1 proliferation relative to control media and these changes were more pronounced with MDA-MB231 conditioned media as compared to media conditioned by MCF-7 cells (FIG. 7A). Similarly, the secretion of VEGF by 3T3-L1 cells was increased upon culture in tumor-conditioned media and this difference was more remarkable with preculture in MDA-MB213 media as compared to MCF-7 media (FIG. 7B).

These results indicate that mammary tumor cells secrete factors that significantly enhance the tumorigenic potential of adipose tissue progenitor cells and that the level of tumor malignancy plays a role in this process.

Figure 8A:
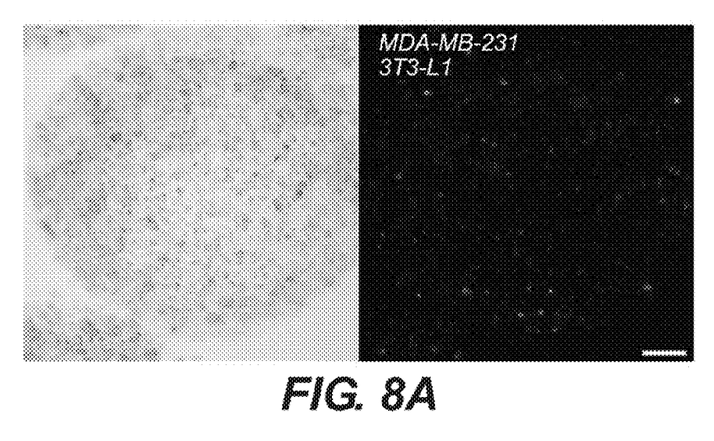
Figure 8B:
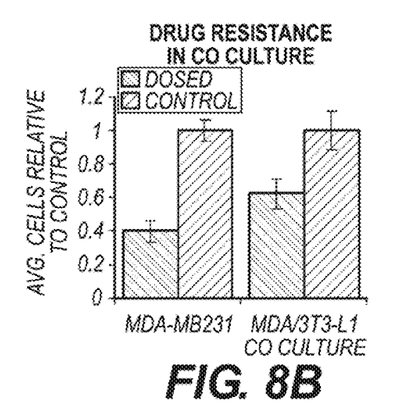
Figure 8C:
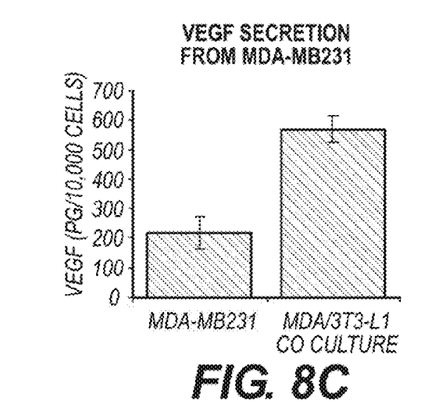
Figure 8D:
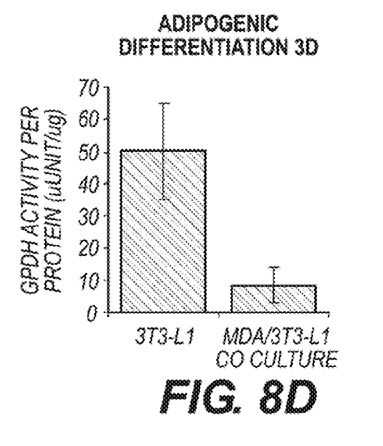
Figure 8E:
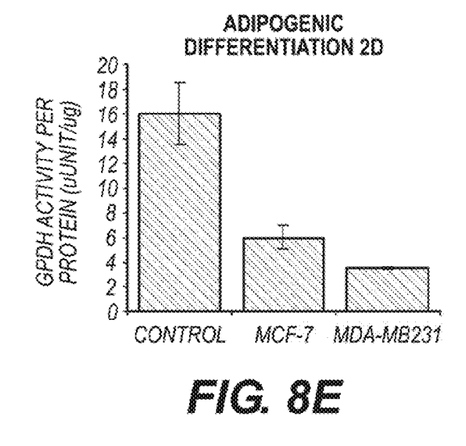

An additional study of MDA-MB231 human breast cancer cells and 3T3-L1 mouse preadipocytes co-cultured in alginate beads (FIG. 8A) further confirms that this system is a more realistic culture system for studying the interaction of cells within the breast tumor microenvironment. When preadipocytes are cultured with the breast cancer cells, the tumor cells are less responsive to chemotherapeutic dosing (FIG. 8B) and exhibit increased secretion of VEGF (FIG. 8C). The function of the preadipocytes within the tumor microenvironment is also altered in that their ability to differentiate is decreased in both 3D co-culture (FIG. 8D) and 2D culture in media conditioned by MCF-7 and MDA-MB231 breast cancer cells (FIG. 8E) as measured by GPDH activity.

In summary, this example shows that breast cancer malignancy represents an integrated function of cell-cell interactions between mammary tumor cells and adipose tissue-derived cells as well as mechanical and soluble microenvironmental cues. Culture models that recreate these interactions in a biomimetic manner are critical for efficient preclinical testing of new anti-cancer drug candidates. Alginate-based 3-D hydrogel systems are used successfully to mimic breast cancer inherent microenvironmental conditions. These data show that 3-D culture of mammary tumor cells within alginate matrices dramatically reduces their responsiveness to chemotherapeutic drugs and better represent the microenvironmental conditions present in tumors in vivo than 2-D cell culture models.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A three-dimensional biomimetic tumor system comprising:
    a first cell of interest;
    a natural or synthetic hydrogel incorporating the first cell of interest, wherein:
    the incorporating hydrogel is crosslinked by chemically mediated crosslinking, ionically mediated crosslinking, thermally mediated crosslinking or photocrosslinking,
    wherein the incorporating hydrogel forms a roughly spherical bead,
    the value for the elastic modulus of the hydrogel is controlled by the extent of crosslinking of the hydrogel, and
    the value for the elastic modulus of the hydrogel is in the range of about E=0.5 kPa to E=100 kPa;
    a second cell of interest of different cell type from the first cell of interest, wherein the second cell of interest is dispersed on, attached to, bound to, disposed or coated on the surface of the hydrogel incorporating the first cell of interest.

2. The biomimetic tumor system of claim 1, wherein the hydrogel is alginate-based.

3. The biomimetic tumor system of claim 1, wherein the diameter of the bead is 100-3000 μm.

4. The biomimetic tumor system of claim 1, comprising a cell adhesion peptide modifying the hydrogel.

5. The biomimetic tumor system of claim 4, wherein the cell adhesion peptide is RGD, YIGSR [SEQ ID NO:1], or a derivative or modification thereof.

6. The biomimetic tumor system of claim 1, wherein the value for the elastic modulus of the hydrogel is about E=0.5-5 kPa, E=5-10 kPa, E=10-20 kPa, E=20-60 kPa, or E=60-100 kPa.

7. The biomimetic tumor system of claim 1, wherein the first cell of interest is selected from the group consisting of a normal cell, benign cell, cancer cell, tumor cell, immortalized cell, genetically engineered cell, stem cell and patient-derived primary cell.

8. The biomimetic tumor system of claim 7, wherein the tumor cell or cancer cell is a breast tumor or cancer cell.

9. The biomimetic tumor system of claim 1, wherein the second cell of interest is selected from the group consisting of a normal cell, benign cell, cancer cell, tumor cell, immortalized cell, genetically engineered cell, stem cell and patient-derived primary cell.

10. A method for making a three-dimensional biomimetic tumor system comprising:
    (a) providing a natural or synthetic hydrogel solution;
    (b) providing an isolated first cell of interest;
    (c) suspending the cell in the hydrogel solution; and
    (d) incorporating the cell in the hydrogel solution by crosslinking the hydrogel,
    wherein step (d) comprises forming the hydrogel into a roughly spherical bead; and
    (e) providing an isolated second cell of interest of a different cell type from the first cell of interest; and
    wherein the second cell of interest is dispersed on, attached to, bound to, disposed or coated on the surface of the hydrogel.

11. The method of claim 10 wherein the hydrogel solution is comprises alginate.

12. The method of claim 11 wherein the cell density is 0-50×10⁶ cells/mL alginate hydrogel solution.

13. The method of claim 10 wherein the diameter of the bead is 100-3000 μm.

14. The method of claim 10 wherein the crosslinking of step (d) is selected from the group consisting of chemically mediated crosslinking, ionically mediated crosslinking, thermally mediated crosslinking and photocrosslinking.

15. The method of claim 10 wherein step (d) comprises extruding the suspended cell in the hydrogel solution into a crosslinking solution.

16. The method of claim 15 wherein step (d) comprises the step of extruding the suspension into isotonic CaCl2.

17. The method of claim 15 wherein the extruding step is performed under coaxial nitrogen flow.

18. The method of claim 10 comprising the step of modifying the hydrogel solution with a cell adhesion peptide prior to step (d).

19. The method of claim 10 wherein the hydrogel solution is 0.5-10% hydrogel.

20. The method of claim 10 wherein the cell density is 0-50×10⁶ cells/mL hydrogel solution.

21. The method of claim 10 comprising pre-coating the hydrogel incorporating the cell of interest with a layer of poly-L-lysine prior to the step of associating the hydrogel with a second cell of interest of different cell type.

22. The method of claim 10 comprising dynamically culturing the incorporated cell of interest.

23. The method of claim 10 wherein the cell of interest is selected from the group consisting of a normal cell, benign cell, cancer cell, tumor cell, immortalized cell, genetically engineered cell, stem cell and patient-derived primary cell.

24. The method of claim 23 wherein the tumor cell or cancer cell is a breast tumor or cancer cell.

25. The method of claim 10 wherein the cell culture system comprises a second cell of interest of different cell type from the first cell of interest.

* * * * *

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Synthetic sequence.

<400> SEQUENCE: 1

Tyr Ile Gly Ser Arg
1               5
```